(12) United States Patent
Cardelius et al.

(10) Patent No.: US 8,663,127 B2
(45) Date of Patent: Mar. 4, 2014

(54) METHOD AND DEVICE FOR DETERMINING A VOLUME RELATED TO THE LUNGS OF A PATIENT

(75) Inventors: Erik Cardelius, Stockholm (SE); Lars Wallén, Spånga (SE); Åke Larsson, Järfälla (SE); Mikael Hanson, Solna (SE); Mattias Holmer, Haninge (SE)

(73) Assignee: Maquet Critical Care AB, Solna (SE)

( * ) Notice: Subject to any disclaimer, the term of this patent is extended or adjusted under 35 U.S.C. 154(b) by 1653 days.

(21) Appl. No.: 11/578,131

(22) PCT Filed: Apr. 7, 2005

(86) PCT No.: PCT/EP2005/051550
§ 371 (c)(1),
(2), (4) Date: Aug. 8, 2007

(87) PCT Pub. No.: WO2005/096934
PCT Pub. Date: Oct. 20, 2005

(65) Prior Publication Data
US 2008/0114262 A1 May 15, 2008

(30) Foreign Application Priority Data
Apr. 8, 2004 (SE) .................................. 0400946

(51) Int. Cl.
*A61B 5/08* (2006.01)
(52) U.S. Cl.
USPC ............................................................ 600/538
(58) Field of Classification Search
USPC ................................................... 600/529–543
See application file for complete search history.

(56) References Cited

U.S. PATENT DOCUMENTS

| 4,941,476 | A |   | 7/1990 | Fisher |
|---|---|---|---|---|
| 5,503,151 | A | * | 4/1996 | Harnoncourt et al. ........ 600/438 |
| 5,540,233 | A | * | 7/1996 | Larsson et al. ................ 600/538 |
| 5,645,071 | A | * | 7/1997 | Harnoncourt et al. ........ 600/532 |
| 5,957,128 | A |   | 9/1999 | Hecker et al. |

(Continued)

FOREIGN PATENT DOCUMENTS

DE 100 38 818 2/2002

OTHER PUBLICATIONS

Newth, et al. "Multiple-breath nitrogen washout techniques: including measurements with patients on ventilators," 1997, Eur. Respir. J. 10: 2174-2185.*

(Continued)

*Primary Examiner* — Navin Natnithithadha
*Assistant Examiner* — Eric Messersmith
(74) *Attorney, Agent, or Firm* — Schiff Hardin LLP

(57) ABSTRACT

A device is directly or indirectly connectable to a patient for determining a volume related to the lungs of the patient. The device has an inspiration part through which a breathing gas passes towards the patient, and an expiration part through which the breathing gas passes away from the patient. The inspiration part has a mouthpiece for introducing a change of the gas composition in the breathing gas. The device implements a method for determining the volume with a detector being arranged in the expiration part that measures a measuring parameter which is dependent on the change in the gas composition, and with a calculation unit connected to the detector unit that determines the variation in the measuring parameter, and determines the volume from the determined variation.

16 Claims, 4 Drawing Sheets

(56) References Cited

U.S. PATENT DOCUMENTS

| | | | |
|---|---|---|---|
| 6,139,506 A | 10/2000 | Heinonen | |
| 6,544,191 B2 * | 4/2003 | Koch et al. | 600/538 |
| 6,629,934 B2 * | 10/2003 | Mault et al. | 600/538 |
| 7,430,924 B2 * | 10/2008 | Gysling et al. | 73/861 |
| 2002/0052560 A1 | 5/2002 | Koch et al. | |
| 2003/0136200 A1 | 7/2003 | Cardelius et al. | |
| 2005/0045175 A1 * | 3/2005 | McCawley et al. | 128/200.14 |
| 2007/0191726 A1 * | 8/2007 | Harnoncourt et al. | 600/532 |

OTHER PUBLICATIONS

Newth et al., "Multiple-breath nitrogen washout techniques: including measurements with patients on ventilators," European Respiratory Journal, vol. 10 (1997), pp. 2174-2185.

* cited by examiner

METHOD AND DEVICE FOR DETERMINING A VOLUME RELATED TO THE LUNGS OF A PATIENT

BACKGROUND OF THE INVENTION

1. Field of the Invention

The present invention concerns a method and an apparatus for determining a volume related to the lungs of a patient.

2. Description of the Prior Art

The lungs are a dynamic organ, which during a breath change volume by the respiratory gas streaming into alveoli (inhalation, inspiration) as well as out of the alveoli (exhalation, expiration). To characterize the different volumes, a number of parameters are accepted. Some of these are: tidal volume, which is a measure of the volume inhaled/exhaled during a normal breath; vital capacity, which is the total volume for a maximal inhalation and a maximal exhalation; functional residual capacity (FRC), which is a measure of the volume remaining in the lungs after a normal exhalation; and ineffective tidal volume, which is a measure of the gas volume which does not contribute to the gas exchange between the lungs and blood circulation during a breath (constituted mainly by the volume in the bronchial branches and the wind-pipe).

In EP 0 653 183, a method and an apparatus useful for determining the functional residual capacity, FRC, is described. One example of the method principally operates in that during a washing-in phase, an inert and non-toxic labelled gas is applied with the respiratory gas during inspiration until an equilibrium in the concentration of labelled gas is obtained in the lungs. The supply is stopped, and by measuring the stream and concentration of labelled gas during a succession of expiration (washing-out phase), the exhaled volume of labelled gas can be determined, which (taking into consideration the dead volumes in the apparatus and the patient) constitutes FRC.

The known method functions well, but obviously requires some special equipment for functioning as required in a clinical environment. To provide all the ventilators, narcotic apparatuses, etc. with complete equipment for supply of a suitable labelled gas and measure the concentration of the same is not economically motivatable, particularly not if the measuring equipment should be able to measure a series of possible labelled gases.

Another factor is that the labelled gases which are to be used clinically must be approved for this use and eventually handled in a special way. Certain gases, such as $SF_6$, are themselves very suitable but result at the same time in requirements on how the gas is handled, even if they were approved for normal clinical use in a hospital. $SF_6$ is for example even a greenhouse gas, and unnecessary release in the atmosphere must be minimized.

SUMMARY OF THE INVENTION

There is therefore a need to provide a method and a device for simple and certain determining of volumes related to the lungs of a patient, particularly FRC.

There is also a desire to provide a method and a device for determining volumes related to the lungs of a patient, particularly FRC, which can be applied directly in a clinical environment without lengthy complications in the existing apparatuses for dosing, measuring or taking into custody specific labelled gases.

The above goals are achieved in accordance with the present invention by a method and an apparatus for determining a volume related to the lungs of a patient wherein, in an inspiration part of the apparatus, a change in a gas composition passing through the inspiration part is initiated and, in an expiration part of the apparatus, a time constant is determined that characterizes the variation in a measurement parameter that is dependent on the change in the gas composition, and a volume related to the lungs of a patient is determined based on this time constant.

The invention is based on the recognition that a change of the inspirational gas composition results in a variable change in the expirational gas composition (until an equilibrium is reached). By determining these variations in a measurement parameter the volume can be determined.

In an embodiment of the method, an ultrasound flow meter is used to perform the determination.

Flow determination with ultrasound is a known technique, even used in medical ventilators (e.g. Servo$^i$, Maquet Critical Care AB, Solna, Sweden). By sending a sound pulse downstream in the flow stream and a sound pulse upstream in the flow stream, a flow speed can be determined (from the difference in duration between downstream and upstream). A non-flow dependent time-of-flight (duration for the sound signal) can be obtained by determining the average for the duration times for upstream and downstream.

The acoustical properties for gases depend among other things on the composition of the gas, e.g. the proportion of oxygen in the respiratory gas. This is used in the present invention. By introducing a change in the composition of the respiratory gas for one or more inspirations, the composition of the expired gas successively changes until an equilibrium state is reached in the lungs. By determining how the successively changed expiration gas affects the sound pulses, a volume determination can be made.

A parameter suitable to use is the non-flow dependent duration (time-of-flight). Since the composition of the gas successively changes during a series of expirations, even the non-flow dependent duration will vary. By determining the time constant for this variation, a volume for the lungs can be determined.

In a modification of this, a fictitious time t' can be used. This is to reduce the influence of variations in the depth of breath and breathing intervals during the measurement of spontaneously-breathing patients. That is because the change in gas composition first is a volume-dependent process and not time-dependent. The fictitious time t' is therefore determined in relation to the total passing stream volume and a taken constant flow.

Alternative examples for use of the ultrasound flow measurer include, for example, determining the variation in gas composition with a gas concentration measurer or with a heat radiation measurer (the variation in gas composition affects the conductivity of heat).

The change in gas composition which is supplied to the breathing gas can consist of a step change, where the change exists during the entire measuring procedure.

Alternatively the change can be performed pulsed, where a large change occurs for one or a few breaths. After that, one returns to the normal gas composition. This results in a lower effect on the patient during the entire measuring procedure.

The change can result in a variation of the oxygen content which, for example, in a step change could result in an increase with 5% oxygen content from a usual level of 30-35%. A pulsed change could constitute an increase from e.g. 21% to 100% for two breaths.

It is evident that even other changes of the gas composition are possible. The changes can relate to some other gas component than oxygen, e.g. laughing gas or xenon (anaesthetic). The change can occur by supplying a specific disturbance gas (as from the state of the technique), e.g. helium. A significant advantage compared with the state of technique is that the actual composition of the gas in reality is irrelevant; it is the variation in a measuring parameter which is important.

To minimize disturbances in the measurements, particularly disturbances which relate to variations in temperature, humidity, etc. (which also can influence the speed of sound), it is suitable to take all measurement data from correlated time points in each expiration, e.g. in the final phase of the expiration.

The device in accordance with the invention can be formed in many different ways and with many complexities. The device can be a handheld tube with a measurement chamber and an ultrasound unit and a mouthpiece for inserting interference in the gas composition. The latter can constitute a capsule filled with compressed gas, e.g. oxygen or helium, which is released during one or a few breaths, after which the variation in the parameter is measured and the volume is determined according to the above.

Alternatively, the device can be a ventilator formed to execute the method.

DESCRIPTION OF THE PREFERRED EMBODIMENTS

Figure 1:
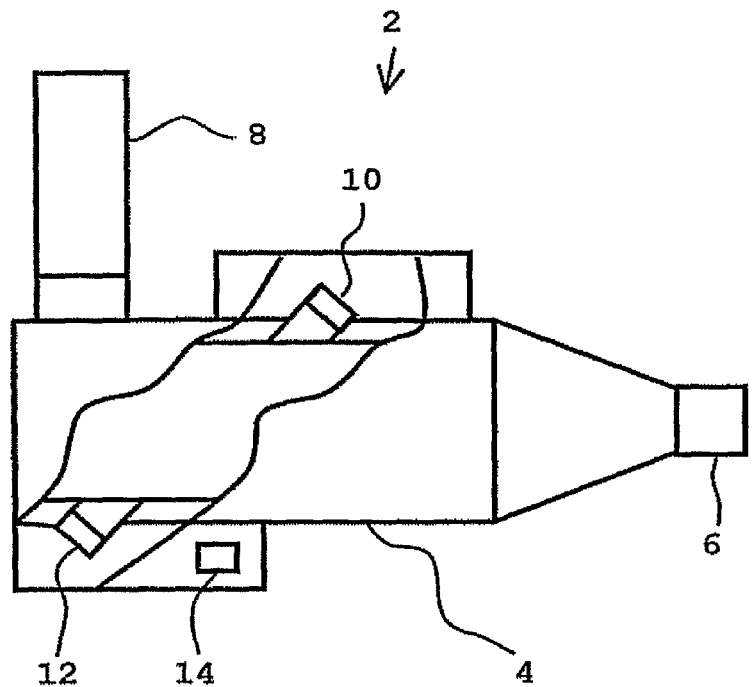
FIG. 1 shows a first example of a device in accordance with the invention.

FIG. 1 shows a hand held test apparatus 2 as a first example of the device according to the invention. The test apparatus 2 has a tube 4 provided with a mouthpiece 6 for a patient to breathe in and out through. In that regard the tube 4 constitutes an inspiration part as well as an expiration part for the test apparatus 2.

It should be noted that "patient" in the present invention has a wide scope which comprises all people and lung-breathing animals for which a volume related to the lungs according to the method described below can be determined.

To determine a volume related to the lungs of a patient, a disturbance must be introduced in the composition of the breathing gas. For the test apparatus 2 the breathing gas consists of regular air. A gas capsule 8 can be connected to the tube to supply a gas which changes the composition of the breathing gas.

The gas capsule 8 preferably contains a compressed gas to minimize its volume and simplify dosing. The gas can constitute oxygen, helium or some other non-toxic gas for which the speed of sound deviates from the speed of sound in the respiratory gas.

The gas in the gas capsule 8 can be released during one or a few breaths. The release can be done by simple ventilation, fixed flow opening, breaking of a membrane, etc., depending on whether the composition shall be changed during a few or more breaths.

In the tube 4 there is also a first transceiver 10 and a second transceiver 12 arranged to determine a non-flow dependent duration (time-of-flight) for sound pulses in expired gas (mean value of upstream duration and down-stream duration, respectively). In this connection the tube 4 constitutes a measuring chamber for the determination. The transceivers 10, 12 can in principle also be replaced with a sound sender and a sound receiver for determining the duration upstream and a second pair of sound sender and sound receiver for determining the duration downstream. Alternatively, a transceiver can be used in one end of the measuring section and a sound reflector in the other. Other arrangements of components can obviously also be used for determining the duration of one or more sound pulses, e.g. by determining the duration perpendicularly to the flow.

The determination of the duration is done during a couple of breaths, during which the gas composition in the lungs returns to normal.

In a calculation unit 14 the actual calculation is made of the volume which is to be determined. The calculation unit 14 can be integrated with the test apparatus 2 as shown in the figure but can also constitute a separate component, which communicates with the test apparatus via cable or wireless.

Figure 2:
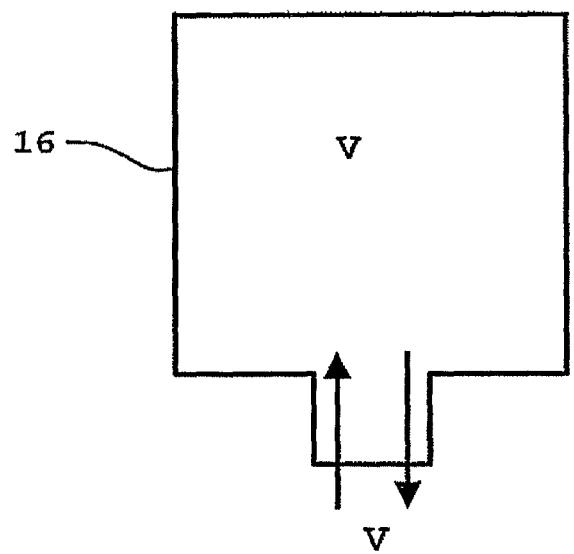
FIG. 2 shows a first model of a lung.

In FIG. 2 a model of a lung is shown from which a calculation model can be described. The lungs correspond to this model of a container 16 with the volume V. The volume V is ventilated with an alveolar flow $\dot{V}_A$. Assuming a good blend in the volume V, the following equation for a change in the oxygen concentration is obtained:

$$\overline{V} \cdot dF_{O_2} = (\dot{V}_A \cdot F_{mix} - \dot{V}_A \cdot F_{O_2}) \quad (1)$$

where V constitutes the mean volume. This has the differential equation:

$$\frac{dF_{O_2}}{dt} = \frac{\dot{V}_A \cdot F_{mix} - \dot{V}_A \cdot F_{O_2}(t)}{\overline{V}} \quad (2)$$

which has the solution:

$$F_{O_2}(t) = \frac{\dot{V}_A \cdot F_{mix}}{\dot{V}_A} + \left[F_{O_2}^{start} - \frac{\dot{V}_A \cdot F_{mix}}{\dot{V}_A}\right] \cdot e^{-\frac{\dot{V}_A}{\overline{V}} \cdot t} \quad (3)$$

Knowing the time constant τ, the mean volume V can be calculated through:

$$\overline{V} = \tau \cdot \dot{V}_A = \tau \cdot (\dot{V}_E - \dot{V}_D) \quad (4)$$

where $V_E$ represents expired minute volume and $V_D$ represents dead volume ventilation. From the mean volume, for example FRC can be determined by subtracting the volume corresponding among others to the dead volume.

The time constant τ can be determined from the change in duration time for the sound pulses through the breathing gas.

Figure 3:
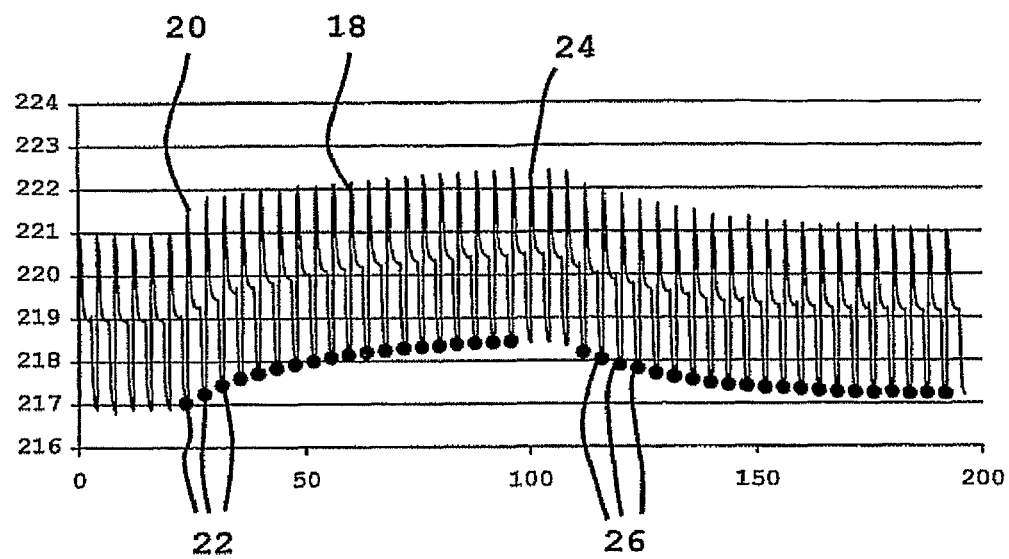
FIG. 3 shows in a diagram a first measurement series when determining a volume.

FIG. 3 shows a measuring series 18 of the duration time for a number of breathing cycles. The duration time varies during the entire breathing cycle, but at breathing cycle 20 a step change is initiated in the breathing gas composition and a lapse curve starts. From a first series of measuring points 22 the time constant τ for the lapse curve can be determined.

The measuring points 22 are correlated to one and the same time point during the respective breathing cycle, i.e. they are taken during practically identical circumstances regarding temperature, humidity, $CO_2$, etc. In that way the measuring points 22 are, as much as possible, independent of all factors which can affect the duration time. In principle, the maximum and/or minimum values could also be used to determine the time constant τ.

At the breathing cycle 24 the gas composition is restored to the original. A second series of measuring points 26 can in this connection be used to execute the same determination once again. The two measurements executed in this way can be used to control the determined volume so as to be appropriate.

If oxygen is used as changing gas in connection with a step change as described above, an undesired effect in the form of modified gas exchange in the lungs can affect the result. To minimize such an effect, a pulsed change of the gas composition can instead be made.

Figure 4:
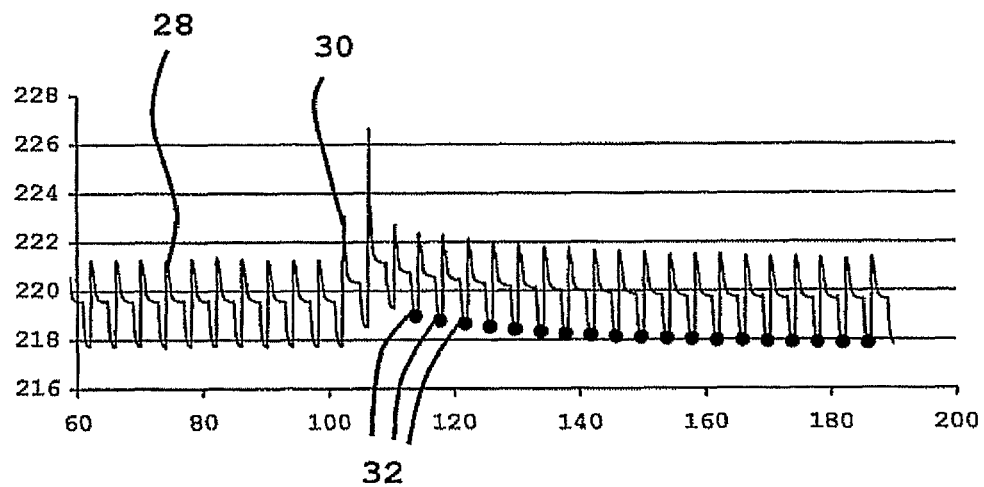
FIG. 4 shows in a diagram a second measurement series when determining a volume.

FIG. 4 shows a measurement series 28 where a pulsed change of the gas composition has been made in breathing cycle 30. The pulsed change constitutes in this case pure oxygen, which is supplied to the patient during two breathing cycles. Subsequently the time constant τ is determined from a series of measurement points 32 in the same way as described above.

The pulse method results in a shorter time with deviating gas composition in the lungs. The pulse method even increases the accuracy in the determination since factors such as physical solubility in blood and metabolistic changes are minimized.

FIG. 2 shows a model to represent the lungs and the ventilation of them. A drawback with the model in FIG. 2 is that it presumes a relatively constant breathing rhythm, i.e. the breathing volume and the breathing interval are constant for each breathing cycle.

Figure 5:
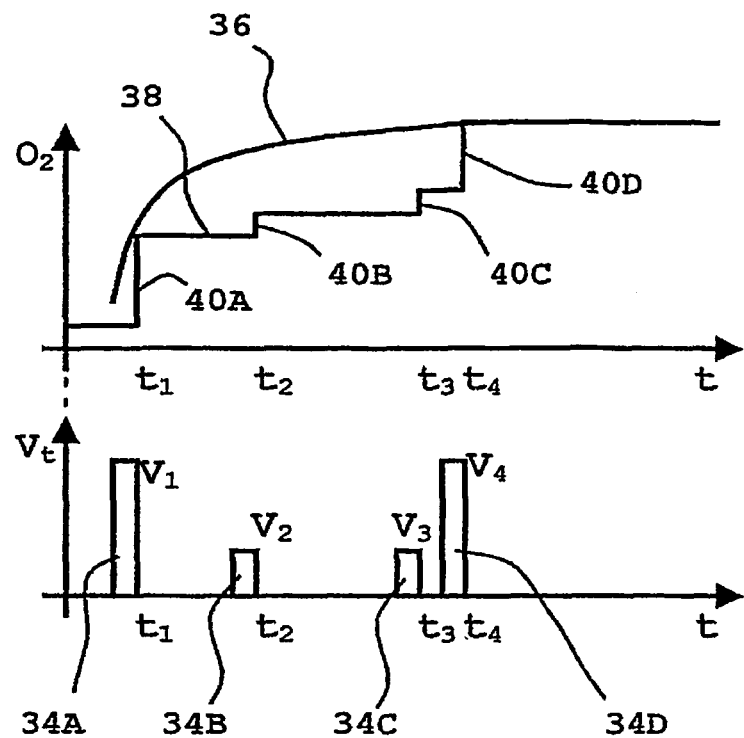
FIG. 5 shows in a diagram how variable breathing volume and variable breathing interval can affect the determination.

FIG. 5 illustrates the effects of a variation in breathing volume and interval for the model according to FIG. 2. An upper graph shows the oxygen change over time, corresponding to the washing-in duration with a changed oxygen concentration. A lower graph shows the tidal volume over time for four breaths 34A, 34B, 34C, 34D. The exponential function 36 in the upper graph shows an ideal change at the washing-in (to determine the time constant τ). The curve 38 shows the actual changes during the four breathing cycles 34A, 34B, 34C, 34D. The actual change of the oxygen concentration depends on the breathing volume. The first breath 34A accordingly results in a first step change 40A in the oxygen concentration. The second breath 34B, which has a considerably lower tidal volume, only results in a small second step change 40B. The third breath 34C occurs after a long pause and also has a low tidal volume. A third step change 40C is therefore also low and occurs after a corresponding time interval. The fourth breath 34D finally occurs short after the third breath 34C and has a larger tidal volume. The corresponding fourth step change 40D will in this connection also be larger and reaches up to the exponential function 36. The washing-in is then done.

It is clear that it is difficult to adapt the curve 38 to the exponential function 36.

Figure 6:
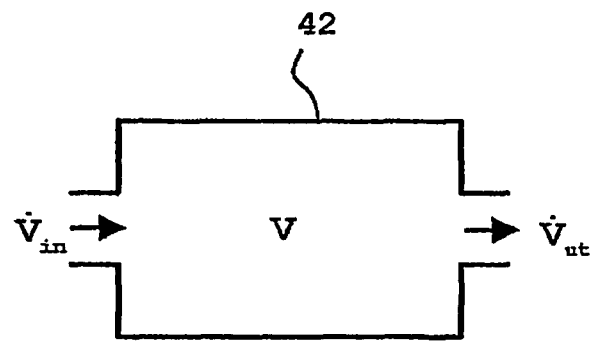
FIG. 6 shows a second model of a lung.

To more easily be able to determine the exponential function and the time constant at the volume determination, instead a model according to FIG. 6 could be used. In this model the lungs again correspond to a container 42. The container has a volume V through which a constant flow $V_{in}=V_{ut}=V$ streams. This means that the washing-in or washing-out duration can be described as follows:

$$F_{O_2}(t) = F_{in} + (F_{O_2}(0) - F_{in}) \cdot e^{-\frac{\dot{V}}{V} \cdot t} \quad (5)$$

By supposing a constant flow, f, and determining the total volume of gas, $V_{tot}$, which is washed through the lungs, a fictitious time, t', can be determined accordingly:

$$t'(n) = \frac{\sum_{i=0}^{n} V_i}{f} \quad (6)$$

The variable fictitious time, t', is going to correspond to the time which had passed if a continuous flow had passed the lungs, i.e. more like the situation which is present at a regular breathing rhythm.

Figure 7:
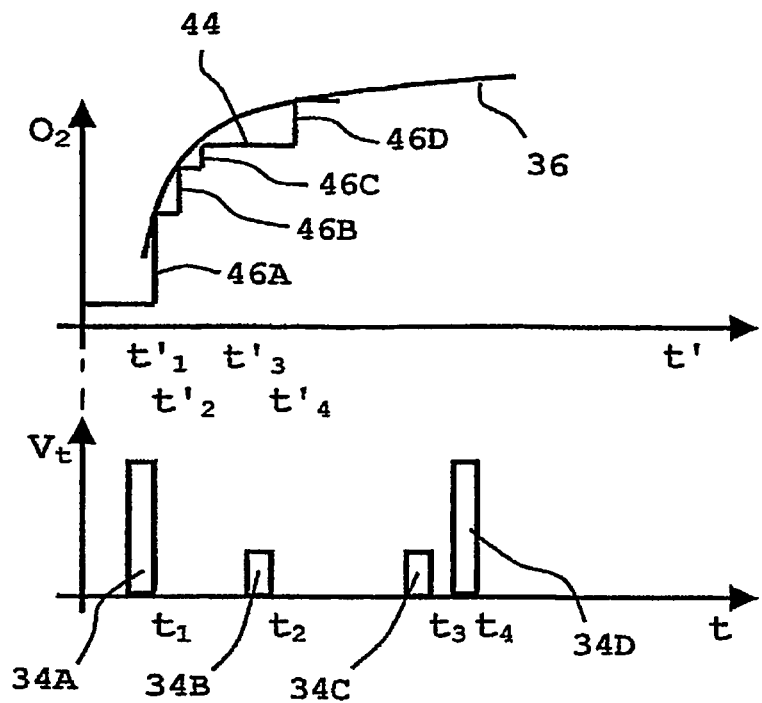
FIG. 7 shows in a diagram how compensating can be done for variable breathing volume and variable breathing interval.

In FIG. 7 upper and lower graphs corresponding to those in FIG. 5 are shown. The lower graph shows the four breaths 34A, 34B, 34C and 34D. The upper graph shows the exponential function 36. The curve 44 shows how the fictitious time t' results in a better adaptation than the curve 38 in FIG. 5. The first breath 34A which occurs at time point $t_1$ corresponds in the fictitious number scheme to a first step change 46A at time point $t'_1$. The second breath 34B at time point $t_2$ had a lesser tidal volume. This corresponds to a second smaller step change 46B at time point $t'_2$. The third breath 34C at time point $t_3$ corresponds in the same way to a third step change 46C at time point $t'_3$, and the fourth breath 34D at time point $t_4$ corresponds to a fourth step change 46D at time point $t'_4$.

It is clearly evident that the curve 44 better corresponds to the exponential function 36 than the curve 38 in FIG. 5.

Figure 8:
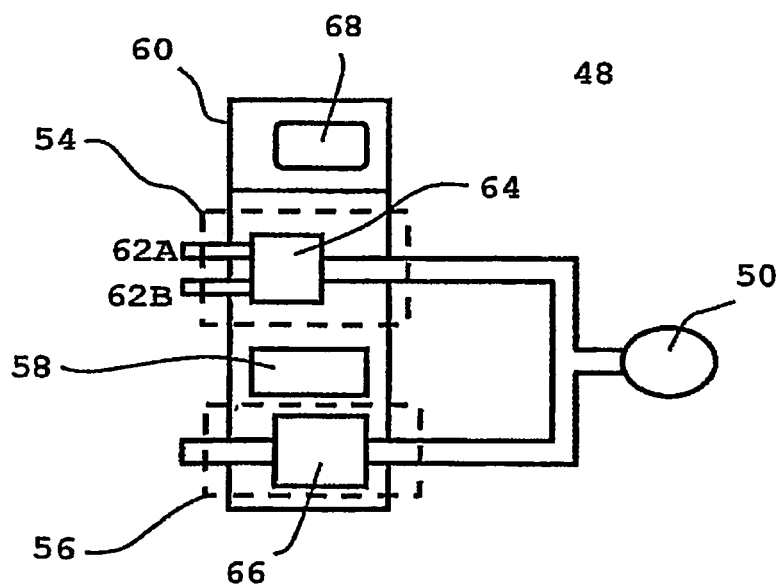
FIG. 8 shows a second example of a device in accordance with the invention.

FIG. 8 shows a second embodiment of a device according to the invention. In this case the device constitutes a ventilator 48 which is connectable to a patient 50 via a hose system 52. The ventilator 48 can, for example, be a modified Servo$^i$, Maquet Critical Care AB, Solna, Sweden.

The ventilator 48 has an inspiration part 54, an expiration part 56, a calculation unit 58 and a user interface 60. In the following all components which can be used in a ventilator are not taken up, but only those which are of significance to perform volume determinations according to the above described processes. A large number of other components are known and could consequently be included in the ventilator 48.

The inspiration part 54 in itself consequently includes, among other things, connections 62A, 62B for gases, e.g. air and oxygen, and a gas regulator 64, which regulates the composition, pressure and flow of the breathing gas. The expiration part 56 has a flow meter 66, which measures flow with ultrasound. The calculation unit 58 can be formed by one or more processors or the like and can include all controlling and watching functions for the ventilator 48. The user interface 60 can have an interactive screen 68 for introduction of breathing modes, initiating the process, etc., and can show measurement data, curves and calculated volumes.

An example of how a volume-determination function for determining FRC can be implemented in the ventilator 48 is that a measurement is initiated by requesting a volume determination via the user interface 60. The calculation unit 58 then controls the gas regulator 64 so that a change in the breathing gas composition is initiated, e.g. in the form of two breaths with 100% oxygen.

In the flow meter the duration time is determined for the sound pulses which are used to determine the flow. From the flow is even received the volume of gas passing out. Out of the duration time measurement, which in principle can be similar to the measurement shown in FIG. 4, measuring points are taken from the same phase in the breathing cycle for a number of breathing cycles. From the measuring points the time constant τ and the mean volume in the lungs are determined. To obtain FRC the dead volume is subtracted (which can be determined in a known manner).

Even if only the ultrasound measurer is explicitly described in the embodiments of FIG. 1 and FIG. 8, respectively, other components could be used in a corresponding way to take the time constant (or corresponding parameter) to perform the volume determination. Gas detectors and heat radiating detectors have been mentioned earlier. Use of these results in equivalent equations and connections between volume and time constant.

We claim as our invention:

1. A method for determining a volume related to the lungs of a patient, comprising the steps of:
    supplying breathing gas to the lungs of a patient with an apparatus having an inspiration part, through which said breathing gas passes prior to introduction into the patient and an expiration part through which expired breathing gas from the patient passes, said lungs being ventilated with an alveolar flow, and exhibiting a functional residual capacity (FRC) that is a volume remaining in the lungs following a normal exhalation;
    in said inspiration part, initiating a change in gas composition of said breathing gas passing therethrough;
    in said expiration part, measuring a parameter that exhibits a variation dependent on said change in said gas composition of said breathing gas, and determining a time constant that characterizes said variation; and
    in a processor, determining said FRC of the lungs of the patient from a multiplication product consisting of a first multiplicand consisting of said alveolar flow and a second multiplicand consisting of said time constant.

2. A method as claimed in claim 1 wherein said expiration part comprises a measurement chamber, and wherein the step of measuring said parameter comprises emitting a series of acoustic pulses into said measurement chamber and measuring said parameter dependent on said series of acoustic pulses caused by said change in said gas composition.

3. A method as claimed in claim 2 comprising measuring time-of-flight of said acoustic pulses as said parameter.

4. A method as claimed in claim 1 comprising measuring a gas concentration of a component in the changed gas composition as said parameter.

5. A method as claimed in claim 1 comprising measuring a non-flow-dependent duration of heat radiation between two fixed points in said expiration part as said parameter.

6. A method as claimed in claim 1 comprising changing said gas composition in said inspiration part in steps.

7. A method as claimed in claim 1 comprising changing said gas composition in said inspiration part as a pulse change.

8. A method as claimed in claim 1 comprising determining said time constant from measurement of said parameter at correlated points in time during respective breathing cycles in a plurality of breathing cycles of the patient.

9. A method as claimed in claim 1, comprising measuring said parameter at only one point in time of a breathing cycle of the patient.

10. An apparatus for determining a volume related to the lungs of a patient, comprising:
    a breathing-assist device adapted to interact with a respirating patient to supply breathing gas to the lungs of the patient, said breathing-assist device having an inspiration part, through which said breathing gas passes prior to introduction into the patient, and an expiration part through which expired breathing gas from the patient passes, said lungs being ventilated with an alveolar flow, and exhibiting a functional residual capacity (FRC) that is a volume remaining in the lungs following a normal exhalation;
    in said inspiration part, a component configured to initiate a change in gas composition of said breathing gas passing therethrough;
    in said expiration part, a detector configured to measure a parameter that varies dependent on said change in said gas composition of said breathing gas, and to determine a time constant that characterizes said variation; and
    a calculation unit configured to determine said FRC of the lungs of the patient from a multiplication product consisting of a first multiplicand consisting of said alveolar flow and a second multiplicand consisting of said time constant.

11. An apparatus as claimed in claim 10 wherein said inspiration part comprises a measurement chamber, and wherein said detector is an ultrasound unit that emits and detects acoustic pulses in said measurement chamber.

12. An apparatus as claimed in claim 10 wherein said breathing-assist device is a medical ventilator.

13. An apparatus as claimed in claim 10 wherein said inspiration part and said expiration part comprise a common tube that is directly connectible to the patient.

14. An apparatus as claimed in claim 13 wherein said component configured to initiate said change in the gas composition comprises a capsule containing additive gas, said capsule being releasably connectible to said tube.

15. An apparatus as claimed in claim 10 wherein said detector is configured to measure said parameter at only one point in time of a breathing cycle of the patient.

16. A method for determining a volume related to the lungs of a patient, comprising the steps of:
    supplying breathing gas to the lungs of a patient with an apparatus having an inspiration part, through which said breathing gas passes prior to introduction into the patient and an expiration part through which expired breathing gas from the patient passes, said lungs being ventilated with an alveolar flow, and exhibiting a functional residual capacity (FRC) that is a volume remaining in the lungs following a normal exhalation;
    in said inspiration part, initiating a change in gas composition of said breathing gas passing therethrough;
    in a processor, calculating a parameter that exhibits a variation dependent on said change in said gas composition of said breathing gas as a fictitious time that would have elapsed if a continuous, constant flow of said breathing gas passed through said lungs, based on a total volume of breathing gas passing through the lungs during at least one patient breathing cycle, and determining, from said fictitious time, a time constant that characterizes said variation; and
    in said processor, determining said FRC of the lungs of the patient from a multiplication product of said alveolar flow and based on said time constant.

* * * * *